United States Patent [19]

White et al.

[11] 4,237,306

[45] Dec. 2, 1980

[54] THALLIUM(III) REAGENTS SUPPORTED ON MONTMORILLONITE CLAY MINERALS AND OXYTHALLATION PROCESSES FOR UTILIZING SAME

[75] Inventors: John F. White, Ridgewood; Edward C. Taylor; Chih-Shu Chiang, both of Princeton, all of N.J.

[73] Assignee: Emery Industries, Inc., Cincinnati, Ohio

[21] Appl. No.: 38,030

[22] Filed: May 10, 1979

Related U.S. Application Data

[62] Division of Ser. No. 838,312, Sep. 30, 1977, Pat. No. 4,172,955, which is a division of Ser. No. 718,068, Aug. 26, 1976, Pat. No. 4,607,823.

[51] Int. Cl.³ .............................................. C07C 9/76
[52] U.S. Cl. ...................................... 560/105; 560/59; 560/55
[58] Field of Search ........................... 560/105, 59, 55

[56] References Cited

PUBLICATIONS

McKillop, A. et al., J.A.C.S. 95:10, 3340-3343.

*Primary Examiner*—Paul J. Killos
*Attorney, Agent, or Firm*—Kenneth D. Tremain

[57] ABSTRACT

Improved supported thallium(III) reagents are provided which significantly improve reaction rates and product selectivity of oxythallation reactions. The present reagents have a thallium(III) salt of an acid on the surface and within montmorillonite clay minerals.

4 Claims, No Drawings

THALLIUM(III) REAGENTS SUPPORTED ON MONTMORILLONITE CLAY MINERALS AND OXYTHALLATION PROCESSES FOR UTILIZING SAME

The U.S. Government has rights in this invention pursuant to Grant No. CHE 72-00427 awarded by the National Science Foundation.

This is a division of pending application Ser. No. 838,312, filed Sept. 30, 1977, now U.S. Pat. No. 4,172,955, which is a division of application Ser. No. 718,068, filed Aug. 26, 1976, now U.S. Pat. No. 4,607,823.

BACKGROUND OF THE INVENTION

The deposition of thallium salts, such as the nitrate, on support materials is known. U.S. Pat. No. 3,157,688 discloses supported catalysts containing thallium ion and the use of these catalysts for the preparation of nitriles by the reaction of nitric oxide and alkyl-substituted organic compounds containing at least one alkyl group directly attached to a carbon atom which in turn is bonded to another carbon atom by a double bond. The thallium has an oxidation state of at least +1 and the supports have high porosity, low surface area and low cracking activity.

More recently in Netherlands Pat. No. 7,506,546 the deposition of thallium trinitrate on an inert solid carrier and the use of these reagents for the conversion of 6-methoxy-2-propionylnaphthalene to an alkyl ester of 2-(6-methoxy-2-naphthyl)propionic acid has been disclosed. Suggested supports include Florisil ®, neutral alumina and silica gel. McKillop in the Journal of Pure and Applied Chemistry, 43, 463–479 (1975) reports the deposition of thallium trinitrate on celite, neutral and basic alumina, charcoal and Florisil ® and the use of these TTN/support systems for oxidative rearrangement of alkyl aryl ketones to methyl arylacetates.

SUMMARY OF THE INVENTION

We have now discovered a new class of extremely useful thallium(III) supported reagents and quite unexpectedly found that it is possible to obtain markedly improved reaction rates and product selectivity in certain oxythallation reactions. Surprisingly, with reagents of this invention it is often possible to obtain very rapid and in some cases essentially instantaneous reactions and essentially complete conversion of the starting materials to the desired product.

The invention relates to improved thallium-containing compositions, referred to herein as supported oxythallation reagents, comprising a montmorillonite support material and a thallium salt. More specifically, the invention deals with supported thallium salts where virtually all of the thallium is present in the +3 oxidation state and wherein said salts are deposited on the surface and within the lattice of the montmorillonite clay.

The clay minerals useful for the preparation of the supported oxythallation reagents include montmorillonite and other clay minerals from the montmorillonite group as well as those clay minerals, such as bentonite, which have montmorillonite as the predominant constituent. The supported oxythallation reagents contain from about 0.5 to 50 wt. percent, and more preferably, from about 2 to 30 percent by weight thallium, at least 75% of which is in the +3 oxidation state. The supported reagents are obtained by combining a thallium salt of an acid with the montmorillonite clay mineral. An especially useful thallium salt for this purpose is thallium(III) trinitrate trihydrate. Particularly useful supported oxythallation reagents are obtained by depositing thallium trinitrate on acid-activated montmorillonite clays having an acidity greater than 10 and a surface area greater than 200 m$^2$/gram.

DETAILED DESCRIPTION

Oxythallation reactions, including oxidation and oxidative rearrangement, are well-known and described in the literature. These reactions involve the addition of an inorganic thallium(III) salt to unsaturated organic substrates such as olefins, acetylenes, ketones, aldehydes or other compounds containing a carbonyl moiety or compounds containing a carbon-nitrogen double bond. The thallium(III) salts being electrophiles react at the unsaturation which can be present per se or formed in situ. The resulting organothallium adduct is unstable and is a highly reactive intermediate which undergoes rapid decomposition at the C-Tl bond to give a thallium(I) salt and a carbonium ion or carbonium ion-like species, the ultimate fate of which depends on the nature of the anions present from the metal salt, the structure of the organic substrate and the reaction conditions, particularly the solvent.

The present invention relates to improved supported reagents useful in oxythallation reactions. The thallium on the support is predominantly present in the +3 oxidation state. The supports for this invention are naturally occurring clay minerals of the montmorillonite type. For the purpose of this invention and as used herein the term montmorillonite or montmorillonite clay mineral includes the specific clay mineral, other clay minerals from the montmorillonite group and clays such as bentonite which have montmorillonite as the predominant constituent. These clay minerals may be used as obtained from the natural state or activated prior to use such as by acid treatment.

The montmorillonites are crystalline clay minerals of the three-layer type and have an expanding lattice structure. These clays have a laminar or sheet structure wherein the repeating layers consist of two silica tetrahedra and a central alumina octahedra. The layers are continuous in one direction and stacked one above the other in the other direction. The laminar nature of the montmorillonite makes it possible for water and other polar molecules, including organic molecules, to enter between the layers causing the lattice to expand, i.e. the distance between the layers to increase. Charge deficiencies often exist in the lattice of montmorillonites as a result of substitution (exchange) between ions of unlike charge. The charge deficiencies within these clays can be balanced by the adsorption of cations (e.g. Na$^+$, K$^+$, Ca$^{++}$ and in this instance Tl$^{+++}$) which at least partially accounts for the effectiveness of the montmorillonites as support materials for the present invention. Illustrative mineral clays useful as supports for the oxythallation reagents of this invention include montmorillonite, beidellite, nontronite, hectorite, saponite, sauconite, volkhonskoite, medmontite, pimelite and the various montmorillonite-rich minerals, such as bentonite, and the like.

As previously indicated the supported oxythallation reagents of this invention have thallium(III) ions on the surface and within the montmorillonite structure as a result of contacting the support and the thallium(III)

salt usually in a suitable medium. Useful mediums for this purpose are those in which the Tl(III) salt is at least partially soluble and in which the support can be readily suspended without agglomeration of the support particles. To be useful as a reagent for oxythallation reactions it is necessary that the thallium ions be predominantly in the +3 oxidation state since in such reactions the reagent must function as an oxidizing agent. If the total thallium ion concentration is present in the reduced (thallous) state it is apparent that the supported materials will not function as an oxidant and oxythallation reagent. Accordingly, while small amounts of thallous ion can be present the amount should generally not exceed about 25% of the total thallium ion concentration and it is most desirable that as much of the thallium as possible be in the +3 oxidation state. The thallium (III) salt may be adsorbed or deposited as such on the montmorillonite support and may be associated with a solvent, e.g. methanol.

To obtain useful supported oxythallation reagents having essentially all of the thallium ion in the +3 oxidation state generally requires that special precautions be taken to assure that oxidizable materials are not present during the preparation of the reagent, either on the support, from the medium used or from other sources. Also, it has been found that for best results the support material should not contain excessive amounts of water and the medium used for the preparation should be one in which the thallium(III) salt is readily soluble.

Mixtures of methanol and trimethyl orthoformate have been found to be extremely useful media for the preparation of the supported oxythallation reagents of this invention, particularly if the thallium salt is thallium trinitrate. Some methanol will generally also be present on the support and associated with the thallium salt when the reagent is prepared in a methanol/trimethyl orthoformate medium and these solvated, i.e. methanolated, forms can in fact be advantageous.

While thallium trinitrate (having three waters of hydration associated therewith) is particularly useful for the preparation of the present supported oxythallation reagents other thallium(III) salts can be employed. In general, thallium salts of Brønsted acids whose conjugate bases are weakly nucleophilic such as nitric acid, sulfuric acid, perchloric acid, fluoroboric acid, trifluoroacetic acid, trifluoromethanesulfonic acid, alkyl or aryl sulfonic acids and phosphoric acid are useful. Thallium salts of this type which can be deposited on montmorillonite supports are thallium(III) sulfate, thallium(III) perchlorate, thallium(III) acetate, thallium(III) trifluoroacetate, thallium(III) phosphate and the like.

Especially useful supported reagents are obtained using thallium trinitrate trihydrate and acidic montmorillonite clays having surface areas greater than 200 m$^2$/gram. Even more preferred supported oxythallation reagents are prepared using montmorillonites having an acidity greater than 10 (milliequivalents NaOH/100 grams montmorillonite). Preferred oxythallation reagents exhibiting marked rate enhancement are obtained using Tl(NO$_3$)$_3$.3H$_2$O and acidic montmorillonite with a surface area greater than 250 m$^2$/gram and acidity from about 15 to 100, particularly if the thallium is adsorbed or deposited on the support from a mixture of methanol and trimethyl orthoformate.

The amount of thallium present on the montmorillonite support can range from about 0.5 to 50 percent by weight, based on the total weight of the oxythallation reagent, and more generally will be between 2 and 30 weight percent.

The supported reagents of this invention are useful for any oxythallation or thallation reaction and it has quite unexpectedly been found that they significantly increase the rate of reaction and improve product selectivity of many of these reactions as compared to the previously reported supported thallium reagents. These and other highly desirable features will be evident from the following examples which illustrate just a few of the reactions possible using supported thallium reagents and point out the improved results obtained with the present montmorillonite supported Tl(III) reagents. In these examples all parts and percentages are on a weight basis unless otherwise indicated.

EXAMPLE I

To a glass flask equipped with a magnetic stirrer and powder funnel was added 49 grams (0.11 mole) thallium trinitrate.3H$_2$O, 125 mls trimethyl orthoformate and 100 mls methanol. The mixture was stirred to dissolve the thallium trinitrate and then 110 grams of an acidic montmorillonite clay powder (commercially available K-10 Girdler ® catalyst, Girdler Chemicals, Inc.) having a surface area of 268 m$^2$/g (BET method) and bulk density of 373 g/l introduced with continued stirring. The support had an acidity (total) of 32.8. This was determined using an ion exchange technique employing calcium acetate. End points were determined potentiometrically with 0.5 N NaOH to pH 7.8 which corresponds to the first slight trace of pink color of phenolphthalein indicator. A slight exotherm was observed. After rinsing the powder funnel with 25 mls methanol the resulting slurry was stirred for five minutes and the solvent removed using a rotary evaporator (bath temperature 60°-70° C.; 15-20 mm Hg.). In about 75 minutes solvent removal was complete and 170 grams of a fine, tan-colored free-flowing powder was recovered and stored for subsequent use. Analysis (atomic absorption) indicated there was about 14 weight percent thallium present on the support essentially all of which was in the +3 oxidation state (determined by conventional redox titration).

EXAMPLE II

In accordance with the procedure described in Example I, supported oxythallation reagents were prepared using other montmorillonite clays. One millimole Tl(NO$_3$)$_3$.3H$_2$O was used per 10 grams of the support material. Supports employed were as follows:

| PRODUCT | SUPPORT |
|---|---|
| IIA | Acid-treated montmorillonite (Girdler ® Catalyst K-306, acidity 12.8, surface area 250 m$^2$/g, bulk density 650 g/l, Girdler Chemicals, Inc.). |
| IIB | Activated montmorillonite clay adsorbent (Super Filtrol Grade 1, acidity 42.3, surface area 275 m$^2$/g, Filtrol Corporation). |
| IIC | Southern bentonite (Panther Creek Clay, American Colloid Co.). |

EXAMPLE III

To demonstrate the ring contraction observed when cycloalkenes are oxythallated and the improved results obtained using the montmorillonite supported thallium reagents of this invention the following experiment was conducted: Cyclohexene (0.01 mole) was added to a suspension of 0.01 mole of the supported reagent of Example I in 40 mls carbon tetrachloride while cooling the reaction vessel in an ice-water bath. The reaction was very rapid and all the thallium(III) was reduced after only one minute. The reaction mixture was filtered and the filtrate washed with ether, neutralized with sodium bicarbonate, water-washed and dried over anhydrous magnesium sulfate. Evaporation of the solvent gave 85% yield of cyclopentanecarboxaldehyde dimethylacetal which was confirmed by gas-liquid chromatographic analysis (GLC) and nuclear magnetic reasonance spectroscopy (NMR). There was no detectable thallium in the product.

To emphasize the remarkability of the above results and the superiority of the supported reagents of this invention the reaction was repeated using a supported reagent prepared with Florisil ®, a commercially available magnesium silicate adsorbent manufactured by Floridin Co. Except for the support material used the reagent was prepared identically to the supported reagent of Example I. The resulting Florisil ® supported reagent was evaluated in the above reaction and after one hour only 30% of the desired cyclopentanecarboxaldehyde dimethylacetal was obtained. The remainder of the cyclohexene was converted to undesirable by-products.

EXAMPLE IV

Cinnamaldehydes can be rearranged to the corresponding arylmalondialdehyde tetramethylacetals using supported thallium reagents. To demonstrate the improved results obtained using the supported oxythallation reagents of this invention 0.02 mole cinnamaldehyde was added to a suspension of 0.02 mole of the supported reagent of Example I in 70 mls carbon tetrachloride. Reaction took place immediately as evidenced by a slight exotherm and a change in the color of the mixture from yellowish-green to pale yellow. After one minute the test for thallium(III) was negative. After five minutes the reaction mixture was diluted with chloroform, filtered and the clay washed with chloroform and then ether. The resulting filtrate was extracted with sodium bicarbonate solution, water and then dried over anhydrous magnesium sulfate. Evaporation of the solvent gave 100% yield of a single product identified by GLC and NMR as phenylmalondialdehyde tetramethyl bisacetal. When the above experiment was repeated using oxythallation reagents IIA and IIB similar reactivity was observed and 100% conversion of cinnamaldehyde to phenylmalondialdehyde tetramethyl bisacetal was obtained in five minutes.

For comparative purposes the rearrangement reaction was also conducted using the oxythallation reagent supported on Florisil ® reported in Example III. The Florisil ® supported reagent gave essentially no rearrangement after five minutes and after two hours only 30% conversion of the cinnamaldehyde was obtained. GLC and NMR analysis indicated that the product was a complex mixture with only a small portion being the desired phenylmalondialdehyde tetramethyl bisacetal.

EXAMPLE V

Following a procedure similar to that described in Example IV, 0.01 mole p-methoxycinnamaldehyde was reacted with 0.01 mole of the supported reagent of Example I in 40 mls carbon tetrachloride. The reaction was virtually instantaneous and essentially all of the thallium(III) was reduced after one minute. Work-up of the reaction mixture and analysis of the reaction product by GLC and NMR indicated that p-methoxyphenylmalondialdehyde tetramethyl bisacetal was obtained in 100% yield.

EXAMPLE VI

Following the procedure of Example IV, 0.01 mole α-methylcinnamaldehyde and 0.01 mole of the supported reagent of Example I were reacted in carbon tetrachloride. 100% Yield of crude phenylmethylmalondialdehyde tetramethyl bisacetal (b.p. 101°–102° C./0.2 mm Hg.) was obtained.

EXAMPLE VII

The versatility of the supported oxythallation reagents of this invention is further demonstrated by the following reaction wherein styrene is rearranged to phenylacetaldehyde dimethylacetal. To achieve rearrangement 10.4 grams (0.1 mole) styrene in 25 mls of hexane was added to a glass reaction vessel containing 0.01 mole of the supported reagent of Example I suspended by mechanical agitation in 400 mls hexane. This mixture was stirred for 30 minutes with cooling and the reaction mixture filtered. There was no detectable thallium in the filtrate which was neutralized with sodium bicarbonate solution, washed with water and then dried over anhydrous magnesium sulfate. The crude product remaining after evaporation of the solvent was distilled (68°–70° C./0.2 Torr) to obtain pure phenylacetaldehyde dimethylacetal. 15.3 Grams (92% yield) phenylacetaldehyde dimethylacetal was obtained.

EXAMPLE VIII

Using a procedure similar to that described in Example VII, 11.8 grams (0.1 mole) propenylbenzene (β-methylstyrene) was reacted with 0.1 mole of the supported thallium reagent in hexane for 30 minutes to prepare hydratropic aldehyde dimethylacetal. After work-up of the reaction mixture and distillation (85°–86° C./0.1 Torr) of the crude product, 16.5 grams (91% yield) α-methyl phenylacetaldehyde dimethylacetal was obtained.

EXAMPLE IX

To further point out the advantages obtained using the supported oxythallation reagents of this invention reagents prepared using various montmorillonite support materials were evaluated to determine their ability to rearrange acetophenone to methyl phenylacetate. All of the rearrangement reactions were conducted using 0.1 mole of the supported reagent and 12 grams (0.1 mole) acetophenone in 425 mls hexane. The montmorillonite supported reagents used were those of Examples I and II. Reaction times and percent conversions obtained with these reagents were as follows:

| Supported Reagent | Reaction Time (Minutes) | Percent Conversion |
| --- | --- | --- |
| I | 5 | 99 |
| IIA | 5 | 90 |
| IIB | 5 | 90 |
| IIC | 10 | 80 |

For comparative purposes several oxythallation reagents were prepared using non-montmorillonite supports. The procedure of Example I was followed for the preparation of each of these reagents and 44.4 grams Tl(NO₃)₃.3H₂O was combined with 100 grams of the support material in 250 mls of trimethyl orthoformate/methanol (50/50) solution. Support materials employed were graphite, acid-washed graphite, neutral silica-alumina and sulfonated styrene-divinylbenzene resin. When evaluated in the acetophenone rearrangement reaction the following results were obtained:

|  | Reaction Times (Minutes) | Percent Conversion |
|---|---|---|
| Support Materials Used: |  |  |
| Graphite (Ventron Alpha Graphite, 20-60 mesh) | 30 | 75 |
| Acid-washed graphite* | >30 | 50 |
| Silica-alumina (Davison 135) | 90 | 85 |
| Sulfonated styrene-divinylbenzene resin | >30 | 50 |

*Twenty grams Ventron Alpha Graphite (20-60 mesh) were treated with 24 mls conc. HNO₃ for 2 minutes, water washed and dried 14 hours at 380° C.

From the above results it is evident that the reagents prepared using the montmorillonite supports are much superior to those prepared from graphite, acid-washed graphite, silica-alumina and sulfonated styrenedivinylbenzene resin. Much increased rates of reaction are obtained using the montmorillonite supported reagents of this invention; in fact, using the supported reagent of Example I essentially complete rearrangement is obtained in less than 5 minutes.

In the same manner supported reagents were prepared using Florisil®, activated alumina (Alcoa F-1 alumina, 325 mesh) and silica alumina (AERO® 8020, American Cyanamid, pellets ground to 60–100 mesh) as the support materials. Reagents prepared using these latter supports gave large amounts of undesirable by-products when evaluated in the acetophenone rearrangement reaction. Sixty percent conversion of acetophenone was obtained using the Florisil® supported reagent after five minutes reaction; however, only 50% selectivity to methyl phenylacetate was obtained. The activated alumina supported reagent gave 50% conversion of the acetophenone but only 50% selectivity of the methyl phenylacetate. Only 50% selectivity to methyl phenylacetate was also obtained using the silica-alumina supported reagent.

The advantages of the present invention are readily apparent from the above results which point out the superiority of the montmorillonite supported reagents. It is evident from these comparative examples that not only do the montmorillonite supported reagents give very rapid and complete rearrangement but they also give high yields of the desired product, in many cases to the virtual exclusion of undesirable by-products. The combination of rapid reaction rate and high product selectivity is a highly desirable feature not generally obtainable using heretoforeknown oxythallation reagents.

EXAMPLE X 1.7 Grams (0.01 mole) 2-acenaphthone was added to a suspension of 0.02 mole of the montmorillonite supported reagent of Example I in 50 mls carbon tetrachloride. The reaction mixture was agitated for about 20 minutes and the single product recovered in the conventional manner. 88% Yield methyl naphthylacetate, confirmed by NMR and infrared analysis, was obtained.

EXAMPLES XI-XIV

Various substituted acetophenones having the general formula

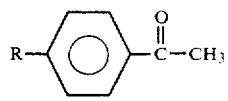

were reacted with the montmorillonite supported reagent of Example I to prepare the corresponding substituted methyl phenylacetates. For these reactions 0.01 mole of the substituted acetophenone was added to a heterogeneous mixture of 0.01 mole of the supported reagent in 40 mls carbon tetrachloride. The recovered crude products, after analysis by GLC and NMR to determine product selectivity, were fractionally distilled and the yield recorded. Results were as follows:

| Example | R | Reaction Time (Minutes) | Selectivity (Percent) | Yield (Percent) |
|---|---|---|---|---|
| XI | F | 5 | 100 | 87.5 |
| XII | CH₃ | 5 | 100 | 84 |
| XIII | CH₃O | 5 | 100 | 91.6 |
| XIV | Br | 30 | 95 | 89 |

EXAMPLE XV

The following experiment was conducted to demonstrate the oxidation of phenylacetylene to methyl phenylacetate using a montmorillonite supported reagent. For the reaction molar equivalents of phenylacetylene and the supported oxythallation reagent of Example I were reacted in carbon tetrachloride. The rapid exothermic reaction was accompanied by a pronounced color change of the reaction mixture. Methyl phenylacetate was obtained in high yield.

EXAMPLE XVI 1.35 Grams (0.02 mole) furan was reacted with 0.02 mole of the supported reagent of Example I in 80 mls carbon tetrachloride. The reaction was essentially complete after five minutes as evidenced by a negative test for thallium(III) and pronounced color change of the reaction mixture. The crude 2,5-dimethoxydihydrofuran (1.95 grams) was distilled (bp 60°-61° C./0.6 mm Hg.) to obtain the pure product in high yield.

EXAMPLE XVII

3-Phenyl-2-pentene (0.01 mole) was reacted with 0.022 mole of the supported reagent of Example I in 80 mls carbon tetrachloride for two hours. Analysis of the crude reaction product indicated 100% yield of a single product having a strong infrared adsorption peak at 1735 cm⁻¹. The crude product was hydrolyzed by refluxing with 15% sodium hydroxide solution for 1½ hours followed by extraction and acidification of the aqueous layer. 1.8 Grams white powder melting at 130°-135° C. and identified as 2-methyl-3-phenylbutyric acid was obtained.

EXAMPLE XVIII

To demonstrate the versatility of this invention a supported oxythallation reagent was prepared following the procedure of Example I and using 4.5 grams Tl(NO₃)₃.3H₂O, 4.5 grams of the acidic montmorillonite support and 25 mls trimethyl orthoformate. After evaporation of the solvent and drying the resulting supported reagent (23% Tl) was slurried with 20 mls carbon tetrachloride and reacted with 1.2 grams acetophenone. The reaction was conducted for 5 minutes after which time the reaction mixture was diluted with chloroform, filtered, washed with sodium bicarbonate solution and dried. Evaporation of the solvent yielded 1.6 grams crude product containing 95% methyl phenylacetate.

EXAMPLE XIX

The advantages of the supported montmorillonite oxythallation reagents of this invention are further evident from this example where 1.86 grams 1-tetralone was reacted with 16.5 grams of the supported reagent of Example I in 40 mls of carbon tetrachloride for one minute. A marked color change of the reaction mixture was observed during this time and the mixture was then diluted with 25 mls chloroform and filtered. The filtrate was neutralized with sodium bicarbonate solution, washed with water, dried over anhydrous magnesium sulphate and evaporated to obtain 2.11 grams crude product which upon analysis was shown to contain 80% of a 1:1 mixture of α-methoxytetralone and methyl indanecarboxylate. Repeating the above experiment using 1.86 grams 1-tetralone and 4.5 grams thallium trinitrate for two minutes in a mixture of 20 mls methanol and 20 mls trimethyl orthoformate gave 2.06 grams crude product; however, only 20% of this product was α-methoxytetralone and methyl indanecarboxylate. The remainder (80%) of the crude product consisted of at least eight unidentifiable co-products.

EXAMPLE XX

2-Benzylidene cyclohexanone (1.86 grams) was reacted with 16.5 grams of the supported oxythallation reagent of Example I in $CCl_4$ for 2 minutes. The reaction mixture was then diluted with 25 mls $CHCl_3$, filtered and worked-up in the usual manner. The crude product (2.1 grams) was distilled and 1.77 grams (83% yield) pure methyl 2-benzylidene-1-cyclopentanecarboxylate (bp 109.5°–110° C./0.03 mm Hg.) obtained.

EXAMPLE XXI

4-Thiochromanone (1.64 grams) was reacted with 16.5 grams of the montmorillonite supported reagent of Example I in 40 mls $CCl_4$ for 5 minutes. 2.7 Grams crude product was recovered and distilled to give 1.9 grams (90% yield) 3,4-dimethoxy-1,2-dihydro-1-thianaphthalene (bp. 92°–94° C./0.01 mm Hg.).

EXAMPLE XXII

Ten millimoles propionphenone and 12 millimoles of the supported reagent of Example I were reacted in 50 mls $CCl_4$ to give 1.80 grams (100% yield) methyl α-methylphenylacetate.

EXAMPLE XXIII

Butyrophenone (10 millimoles) and 12 millimoles of the supported reagent of Example I were stirred in 40 mls $CCl_4$ for 10 hours. The mixture was then diluted with 25 mls chloroform, filtered and the filtrate neutralized, washed, dried over $MgSO_4$ and concentrated to give 1.80 grams (100% yield) chromatographically and spectroscopically pure methyl α-ethylphenylacetate.

EXAMPLE XXIV

Thallium(III) trifluoroacetate was dissolved in 15 mls trimethyl orthoformate and 15 mls methanol and the resulting brownish solution mixed with 10 grams Girdler ® K-10 montmorillonite clay. The solvent was evaporated and the resulting free-flowing powder contained 20.4 wt. percent Tl essentially all of which is in the +3 oxidation state. Ten millimoles of the moisture sensitive supported reagent was then combined with 10 millimoles styrene in 40 mls $CCl_4$ and stirred for one hour. Work-up of the reaction mixture as described in Example VII yielded 2.2 grams crude product confirmed to be 95% phenylacetaldehyde dimethylacetate.

EXAMPLE XXV 9.1 Grams $Tl(SO_4)_3 \cdot 7H_2O$, partially dissolved in a mixture of 15 mls methanol and 15 mls trimethyl orthoformate, was combined with 10 grams acidactivated montmorillonite clay (acidity 32.8) with stirring. A free-flowing dry powder containing 44.9% Tl(III) was obtained after evaporation of the solvent. When ten millimoles of this supported reagent were reacted with 10 millimoles styrene in 40 mls trimethyl orthoformate 72% yield phenylacetaldehyde dimethylacetate was obtained.

In general, by this invention it is possible to conduct much faster and more selective oxythallation reactions. Still another highly desirable feature of oxythallation processes conducted using these montmorillonite supported reagents is the fact that the resulting product(s) contain no detectable thallium. The above examples clearly point out these and other advantages obtained using the present supported oxythallation reagents. It is apparent from the comparative data presented herein that much improved reaction rates are obtained with montmorillonite supported reagents and that, in many cases, it is also possible to obtain improved product selectivity and minimize or completely eliminate the formation of undesirable by-products.

The examples also clearly show the superiority of the montmorillonite supported reagents compared to reagents prepared using other well-known and commonly available support materials. While the precise reason for the effectiveness of the montmorillonite supports is not known it is believed to be attributable, at least in part, to the expanding lattice structure and the acidic nature of these unique laminar clay minerals. These features facilitate and enhance association with the thallium salt which may be present as such or in a solvated form. While the exact nature of this association is not known the thallium, both Tl(III) and Tl(I), is tightly bound to the montmorillonite and when these reagents are employed in oxythallation reactions using non-polar, inert solvents there is no detectable thallium contamination of either the solvent or product when analyzed by atomic absorption.

The versatility of the montmorillonite supported reagents and the adaptibility of these reagents to numerous oxythallation reactions are amply demonstrated by the examples which show their ability to react with a wide variety of organic compounds. In general, the montmorillonite supported reagents are useful in any oxythallation reaction, including both oxidations and oxidative rearrangements, where a nucleophilic organic moiety, such as an organic compound containing olefinic, acetylenic or carbonyl groups or a carbon-nitrogen double bond, is reacted with an electrophilic thallium(III) salt.

Illustrative olefinic compounds with which these supported reagents can be used include styrene and ortho-, meta- or para-substituted styrenes wherein the substituent is a fluoro, chloro, bromo, iodo, methyl, methoxy or trifluoromethyl group, α-methylstyrene, α-ethylstyrene, β-methylstyrene, β-ethylstyrene, 1,2-dihydronaphthalene, 3,4-benz-1-cycloheptene, 1-methylenetetralin, 1-methylene-6-methoxytetralin, 1-methylene-7-methoxytetralin, 1-ethylidenetetralin, 1-methyleneindane, 1-methylene-5-methoxyindane, 1-ethylideneindane, 1-propenylidane, 1-methylene-4-thiatetralin, cyclohexene, cycloheptene, 1-methylenebenzocycloheptene, cyclobutene, 2-vinylnaphthalene, 1-propenylnaphthalene, 2-phenyl-2-butene, 3-phenyl-2-pentene, furan, 2-vinylthiophene and the like. Acetylenic compounds which can be oxythallated, in accordance with this invention include phenylacetylene and substituted derivatives thereof, 6-methoxy-2-naphthyl methyl acetylene, naphthylacetylene, 1-butyne, 2-butyne, 1-heptyne, 4-octyne, and the like.

Carbonyl compounds and α,β-unsaturated carbonyl compounds, including ketones, aldehydes and derivatives thereof, which can be advantageously oxythallated using the montmorillonite supported reagents of this invention include but are not limited to acetophenone, p-fluoroacetophenone, p-methylacetophenone, p-methoxyacetophenone, m-phenoxyacetophenone, p-bromoacetophenone, 3,4-methylenedioxyacetophenone, p-trifluoromethylacetophenone, 2-acetylnaphthalene, 2-acetyl-6-methoxynaphthalene, propionphenone, m-phenoxypropionphenone, p-isopropylpropiophenone, 2-propionylnaphthalene, 1-propionylnaphthalene, 6-methoxy-2-propionylnaphthalene, 6-methoxy-1-propionylnaphthalene, butyrophenone, m-phenoxybutyrophenone, p-isopropylbutyrophenone, 6-methoxy-2-butyrylnaphthalene, cyclopentanone, cyclohexanone, cycloheptanone, 1-tetralone, 1-indanone, 1-benzsuberone, 2-benzsuberone, 2-benzylidenecyclohexanone, 4-thiachromanone, 2-acetylthiophene, cinnamaldehyde and the various ortho-, meta- and para-substituted cinnamaldehydes wherein the substituent is a fluoro, bromo, chloro, iodo, methyl, methoxy or trifluoromethyl group, α-methylcinnamaldehyde, α-ethylcinnamaldehyde, α-pentyl-3,5-dimethoxycinnamaldehyde, β-methylcinnamaldehyde, β-ethylcinnamaldehyde, cinnamic acid esters such as methyl cinnamate, ethyl p-methoxycinnamate and methyl o-fluorocinnamate, methyl 2-thienylacrylate, phenyl vinyl ketone (acrylophenone), phenyl cyclopropyl ketone, chalcone, chalcone dimethyl ketal, p-methylchalcone, p-methoxychalcone, p-methoxychalcone dimethyl ketal, o-methoxychalcone, p'-methylchalcone, o'-fluorochalcone, and the like. Oximes, hydrazones, semicarbazones and thiosemicarbazones of the above-mentioned and other carbonyl compounds similarly can be reacted with the montmorillonite supported oxythallation reagents.

We claim:

1. In an oxythallation process for the oxidative rearrangement of an alkyl aryl ketone to the corresponding methyl aryl alkanoate by reaction with an electrophilic thallium (III) salt, the improvement comprising the use of a supported thallium reagent containing from about 0.5 to 50% by weight thallium at least 70% of which is in the +3 oxidation state, said supported reagent obtained by contacting a thallium (III) salt selected from the group consisting of thallium (III) trinitrate, thallium (III) sulfate, thallium (III) perchlorate, thallium (III) acetate, thallium (III) phosphate and thallium (III) triflouroacetate with a montmorillonite clay mineral having a surface area greater than about 200 m²/g in a mixture of methanol and trimethylorthoformate.

2. The process of claim 1 wherein the alkyl aryl ketone is selected from the group consisting of acetophenone, propiophenone and butyrophenone wherein the aromatic moiety is unsubstituted or substituted with an alkyl, alkoxy, aryl, aryloxy or halogen group.

3. The process of claim 2 wherein the supported reagent contains from 2 to 30 weight percent thallium, the montmorillonite support is an acid activated montmorillonite clay and the thallium salt is thallium (III) trinitrate.

4. The process of claim 3 wherein the montmorillonite clay is selected from the group consisting of montmorillonite, beidellite, nontronite, hectorite, saponite, sauconite, volkhonskoite, medmontite, pimelite and clay minerals wherein montmorillonite is the predominant constituent.

* * * * *